United States Patent [19]

Battrell

[11] Patent Number: 5,221,276
[45] Date of Patent: Jun. 22, 1993

[54] ABSORBENT ARTICLE HAVING A TEXTURED FASTENER

[75] Inventor: Charles F. Battrell, Erlanger, Ky.

[73] Assignee: The Procter & Gamble Company, Cincinnati, Ohio

[21] Appl. No.: 840,576

[22] Filed: Feb. 24, 1992

Related U.S. Application Data

[63] Continuation of Ser. No. 409,499, Sep. 19, 1989, abandoned.

[51] Int. Cl.$^5$ .............................................. A61F 13/15
[52] U.S. Cl. ................................... 604/389; 604/391; 604/358; 428/178; 428/373; 24/304
[58] Field of Search ................ 428/99, 120, 178, 343; 24/304, 306, 442; 604/358, 389–391; 128/DIG. 15

[56] References Cited

U.S. PATENT DOCUMENTS

| Re. 26,151 | 1/1967 | Duncan et al. ................ 128/284 |
| Re. 31,252 | 5/1983 | Terpay ............................ 156/71 |
| 2,499,898 | 12/1946 | Anderson ........................ 24/442 |
| 2,607,348 | 8/1952 | Rossenblatt .................. 604/385.1 |
| 3,138,841 | 6/1964 | Naimer ............................ 24/204 |
| 3,176,364 | 4/1965 | Dritz ................................ 24/306 |
| 3,266,113 | 8/1966 | Flanagin, Jr. ................... 24/204 |
| 3,314,838 | 4/1967 | Erwin ............................ 156/71 |
| 3,331,729 | 7/1967 | Danielson et al. ............ 161/162 |
| 3,526,867 | 7/1970 | Keeler, II ........................ 24/442 |
| 3,703,569 | 11/1972 | Wolkowicz ..................... 264/22 |
| 3,808,648 | 5/1974 | Billarant et al. ................ 24/442 |
| 3,848,594 | 11/1974 | Buell ............................ 128/284 |
| 3,853,129 | 12/1974 | Kozak ............................ 128/287 |
| 3,860,003 | 1/1975 | Buell ............................ 128/287 |
| 3,955,246 | 5/1976 | Tanaka .......................... 24/204 |
| 4,010,753 | 3/1977 | Tritsch ........................ 128/284 |
| 4,023,570 | 5/1977 | Chinai et al. ............... 128/290 R |
| 4,029,876 | 6/1977 | Beatty et al. .................. 526/344 |
| 4,169,184 | 9/1979 | Pufahl ............................ 428/311 |
| 4,216,257 | 8/1980 | Schams et al. ................ 428/93 |
| 4,237,889 | 12/1980 | Gobran ........................ 128/287 |
| 4,282,051 | 8/1981 | Terpay .......................... 156/71 |
| 4,315,508 | 2/1982 | Bolick .......................... 128/289 |
| 4,322,875 | 4/1982 | Brown et al. .................. 24/204 |
| 4,351,784 | 12/1982 | Thomas et al. ................ 264/22 |

(List continued on next page.)

FOREIGN PATENT DOCUMENTS

| 0353972 | 7/1989 | European Pat. Off. . |
| 0388681A2 | 9/1990 | European Pat. Off. . |
| 2153599 | 10/1970 | Fed. Rep. of Germany ...... 211/442 |
| 1232367 | 10/1960 | France ............................ 24/442 |
| 56186 | 1/1967 | German Democratic Rep. ... 24/442 |

OTHER PUBLICATIONS

P. 183 Webster New World 3rd Edition ©1988.

Primary Examiner—Randall L. Green
Assistant Examiner—R. Clarke
Attorney, Agent, or Firm—Steven W. Miller; Jeffrey V. Bamber; Monte D. Witte

[57] ABSTRACT

Disposable absorbent articles such as a diaper or a sanitary napkin having a fastening system comprising a pressure-sensitive adhesive fastener having a textured fastening surface. The pressure-sensitive adhesive fastener comprises a backing web having bulbous surface aberrations projecting from a surface of the web and a layer of pressure-sensitive adhesive coated over and bonded to at least a portion of the surface of the bulbous surface aberrations of the backing web. When the fastening system of the present invention is affixed to a diaper, the overlapping portions of the diaper are maintained in contact with each other while the fastening system prevents separation of the overlapping waist portions because it is able to resist the wearer-generated peel forces encountered during wear and the shear stress encountered when the diaper is worn. Further, the fastening system allows the user to easily refasten and check the diaper for soiling and removing the diaper without rendering the fastening system unrefastenable or the diaper unusable.

24 Claims, 7 Drawing Sheets

U.S. PATENT DOCUMENTS

| | | | |
|---|---|---|---|
| 4,404,243 | 9/1983 | Terpay | 428/62 |
| 4,518,643 | 5/1985 | Francis | 428/131 |
| 4,535,020 | 8/1985 | Thomas et al. | 428/131 |
| 4,578,069 | 3/1986 | Whitehead et al. | 604/370 |
| 4,581,792 | 4/1986 | Spier | 24/575 |
| 4,587,152 | 5/1986 | Gleichenhagen et al. | 428/195 |
| 4,589,876 | 5/1986 | Van Tilburg | 604/385 R |
| 4,615,295 | 10/1986 | Wittkopf | 118/261 |
| 4,655,761 | 4/1987 | Grube et al. | 604/389 |
| 4,681,578 | 7/1987 | Anderson et al. | 604/385 R |
| 4,681,581 | 7/1987 | Coates | 604/391 |
| 4,687,478 | 8/1987 | Van Tilburg | 604/387 |
| 4,690,680 | 9/1987 | Higgins | 604/386 |
| 4,699,622 | 10/1987 | Toussant et al. | 604/389 |
| 4,772,444 | 9/1988 | Curro et al. | 264/557 |
| 4,794,674 | 1/1989 | Mintel et al. | 24/143 R |
| 4,801,298 | 1/1989 | Sorenson et al. | 604/384 |
| 4,834,735 | 5/1989 | Alemany et al. | 604/368 |
| 4,846,815 | 7/1989 | Scripps | 24/442 |
| 4,846,821 | 7/1989 | Lyons et al. | 604/369 |
| 4,869,724 | 9/1989 | Scripps | 604/391 |
| 4,900,320 | 2/1990 | McCoy | 604/389 |
| 4,959,265 | 9/1990 | Wood et al. | 604/389 |
| 4,963,140 | 10/1990 | Robertson et al. | 604/389 |

ABSORBENT ARTICLE HAVING A TEXTURED FASTENER

This is a continuation of application Ser. No. 07/409,499, filed on Sep. 19, 1989, now abandoned.

FIELD OF THE INVENTION

The present invention relates to pressure-sensitive adhesive fasteners which can be repeatedly fastened and unfastened, and, more particularly, to a pressure-sensitive adhesive fastener having bulbous protuberances that permit the fastener to resist shear stress and certain peel forces encountered during use. The invention also relates to a method of making the fasteners and to articles, especially disposable absorbent articles, for which the fasteners are particularly useful.

BACKGROUND OF THE INVENTION

Disposable absorbent articles such as disposable diapers are well-known articles of manufacture which are worn by infants and incontinent persons. Disposable diapers are worn about the lower torso of the wearer and are intended to absorb and contain urine and other body exudates thereby preventing these exudates from soiling, wetting, or otherwise contaminating the articles (e.g., clothing, bedding, etc.) which come into contact with the diaper wearer.

When using a disposable diaper, the diaper user fits the diaper on the wearer and fastens it about the wearer's waist by a fastening system to thereby affect a side closure. Fitting the diaper about the wearer usually requires the front and back waist portions of the diaper to overlap each other. Since proper and sustained fit about the waist and legs of the wearer is vital for optimal performance in terms of minimizing leakage of body exudates out of the diaper, a diaper fastening system must be able to provide an effective side closure in which the front and back waist portions are maintained in an overlapping configuration. As the diaper is worn, forces tend to cause the overlapping portions to shift position relative to each other. In other words, the overlapping portions are subjected to forces which tend to cause the portions to assume a position relative to each other which is different from the position they assume when the diaper is initially fitted to the wearer. Unless such shifting is limited, the fit and containment characteristics of the diaper are degraded as the diaper is worn. Thus, the fastening system must be designed to securely engage so it does not separate due to the peel forces and shear stress encountered by the fastening system during use.

As used herein, the term "shear stress" refers to the distributed forces acting tangentially to the surface of contact of the members of the fastening system. During the wearing of a diaper, shear stress tends to cause the members of the fastening system to shift with respect to each other. Shear stress is to be distinguished from "peel forces" which act on the members of the fastening system so as to separate and disengage from each other. A disposable diaper is typically subjected to peel forces in at least three ways. Peel forces are generated by the movements of the wearer during use as they tend to cause the first and second members of the fastening system to pull away from each other, by the wearer in trying to unfasten the fastening system during wear (this being a special problem for disposable diapers worn by infants because infants should not be able to unfasten and remove the diaper on their own), and by the user to check the diaper for soiling or to remove the diaper from the wearer. Because the fastening system should be able to be checked and removed by the user and because the user generated peel forces are much higher than the peel forces generated by the first two methods, the fastening system is preferably designed to have a resistance to peel forces (peel resistance) with respect to only the movement and wearer generated methods. Therefore, the peel resistance should only be great enough to prevent failure of the fastening system during the first two methods but low enough to allow the user to check the diaper for soiling or to remove the diaper from the wearer without undue difficulty or tearing of other members of the diaper.

Therefore, it is desirable to design a fastening system capable of resisting shear stress and peel forces generated by the wearer but having a peel resistance low enough to allow the user to easily remove the diaper or check the diaper for soiling.

Typically, fastening systems have been provided which have adequate shear force resistance to prevent the panels from shifting with respect to each other. However, because the shear forces are so high, the peel resistance of the fastening system is also very high. This is generally the situation because as the coat weight of the adhesive on the smooth surface of the backing web of the fastener is increased to improve the shear force resistance of the fastener, the peel force resistance also rapidly increases. The result is that typical fastening systems may rip the backsheet of the diaper during the process of unfastening it to check if the diaper has been soiled or to adjust its fit, thereby leaving a hole in the backsheet of the diaper and rendering the fastener unrefastenable and the diaper unuseable, due to the high peel resistance of the fastener. Thus, it would be advantageous to provide a fastening system having a high enough shear resistance to prevent the panels from shifting with respect to each other and sufficient peel resistance to prevent failure of the fastening system by the wearer's movements but a peel resistance low enough to allow the user to easily remove the diaper and check for soiling or fit without rendering the fastening system unrefastenable or the diaper unuseable.

It is, therefore, an object of the present invention to provide a unique pressure-sensitive adhesive fastener.

It is also an object of the present invention to provide a pressure-sensitive adhesive fastener having a textured surface.

It is a further object of the present invention to provide a pressure-sensitive adhesive fastener capable of resisting relatively high shear stress while having a desired peel resistance.

It is still a further object of the present invention to provide a fastening system utilizing the pressure-sensitive adhesive fastener of the present invention.

It is an even further object of the present invention to provide a disposable absorbent article such as a diaper having a fastening system that maintains the fit of the diaper at the wearer's waist and legs during wear and that is able to resist peel forces and shear stress encountered during use while allowing the user to easily check the diaper for soiling or to remove the diaper without rendering the fastening system unrefastenable or the diaper unuseable.

These and other objects of the present invention will be more readily apparent when considered in reference to the following description and when taken in connection with the accompanying drawings.

SUMMARY OF THE INVENTION

According to the present invention, a pressure-sensitive adhesive fastener has a textured fastening surface so as to have a relatively high shear resistance and a desired peel resistance. The pressure-sensitive adhesive fastener comprises a backing web having bulbous surface aberrations projecting from a surface of the web and a layer of pressure-sensitive adhesive coated over and bonded to at least a portion of the bulbous surface aberrations of the backing web.

In addition, the present invention relates to a fastening system using the pressure-sensitive adhesive fastener of the present invention. While the fastening system may take many forms, the fastening system preferably comprises a first member comprising the pressure-sensitive adhesive fastener and a landing member engageable with the pressure-sensitive adhesive fastener. The landing member has a textured surface, preferably a surface that allows nesting of the bulbous surface aberrations of the first member with the textured surface of the landing member, so that the desired properties of the fastener are obtained.

Further, the present invention relates to disposable absorbent articles such as a diaper or a sanitary napkin having a fastening system according to the present invention. The diaper fastening system affixes the overlapping portions of the diaper to each other and maintains them in contact with each other during use. The fastening system prevents separation of the overlapping waist portions because the fastening system is able to resist the wearer-generated peel forces encountered during wear and the shear stress encountered when the diaper is worn. Further, the fastening system allows the user to easily refasten and check the diaper for soiling and remove the diaper without rendering the fastening system unrefastenable or the diaper unuseable.

DETAILED DESCRIPTION OF THE INVENTION

While the present invention will be described in the context of providing a fastening system for disposable absorbent articles such as diapers or sanitary napkins, the present invention is in no way limited to such applications. The present invention may, in fact, be practiced to great advantage in any situation wherein a pressure-sensitive adhesive fastener exhibiting the following described characteristics is required. It is believed the detailed description contained herein, which relates to a preferred structure and its use as a fastener on a disposable absorbent article, will allow one skilled in the art to readily adapt the invention to other applications.

Figure 1:
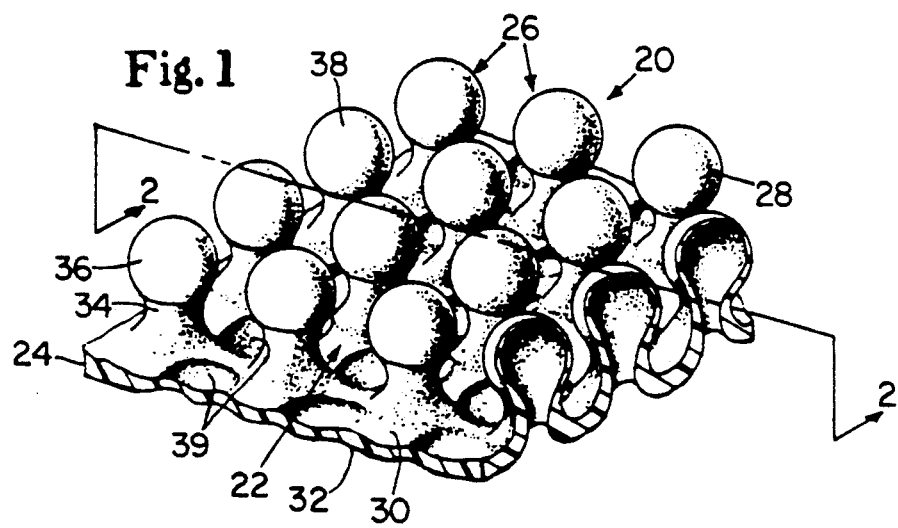
FIG. 1 is a partially cut-away perspective view of a pressure-sensitive adhesive fastener of the present invention.

A preferred embodiment of a pressure-sensitive adhesive fastener 20 having a textured fastening surface 22 according to the present invention is illustrated in FIG. 1. The fastener 20 comprises a backing web 24 having bulbous surface aberrations 26 and a layer of pressure-sensitive adhesive 28 coated over and bonded to at least a portion of the surface of the bulbous surface aberrations 26.

The backing web 24 generally shown in FIG. 1 has a first surface 30 and a second surface 32, and exhibits a pattern of discrete, bulbous surface aberrations 26 projecting from the first surface 30 so as to provide a pressure-sensitive adhesive fastener 20 having a textured fastening surface 22. Each of the bulbous surface aberrations 26 has a base portion 34 and an end portion 36. As used herein, the term "bulbous surface aberration" relates to protuberances having an enlarged, generally rounded or pear-shaped, end portion 36 in comparison to the base portion 34. Thus, the diameter of the bulbous surface aberration 36 in the X axis increases in some plane, $X_2$, in comparison to another plane, $X_1$, as one moves up the vertical Y axis.

The bulbous surface aberrations 26 of the present invention can, thus, have a variety of shapes. The shape of the bulbous surface aberrations 26 can have numerous regular shapes such as a mushroom-like shape or numerous irregular shapes such as an asymmetrical propeller. The end portion 36 of each of the bulbous surface aberrations 26 most preferably comprises at least one microbubble 38. The microbubbled end portion 36 of each bulbous surface aberration 26 comprises a relatively thin, highly flexible, continuous membrane joined about its periphery to the relatively thicker base portion 34 originating in the plane of the backing web 24.

Figure 2:
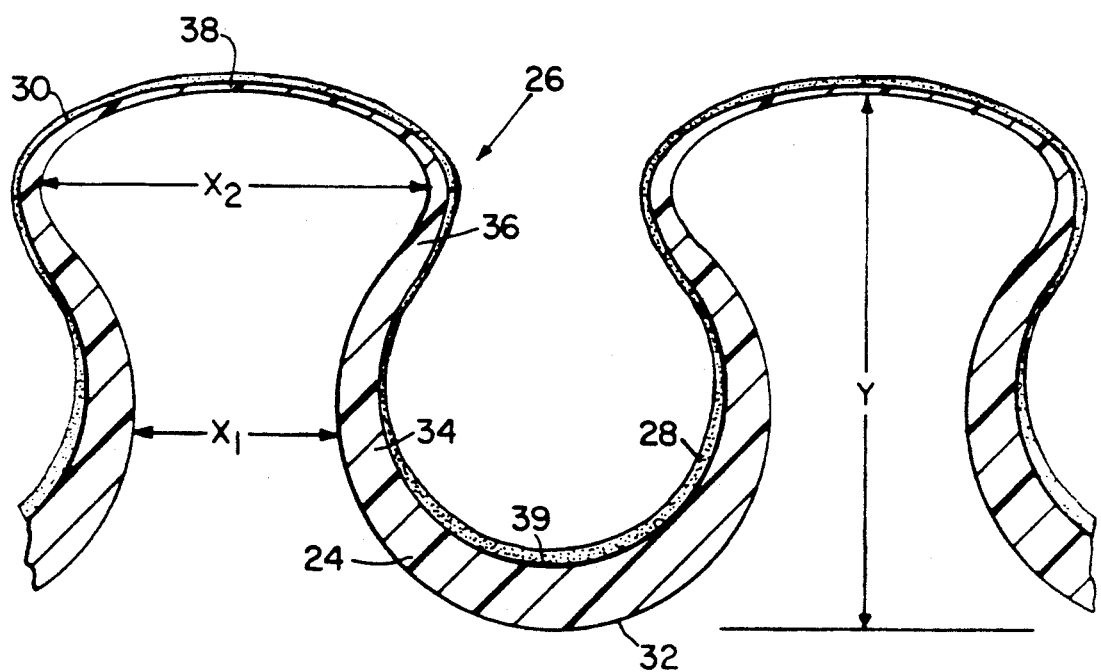
FIG. 2 is an enlarged fragmentary sectional view taken along line 2—2 of FIG. 1.
Figure 3:
FIG. 3 is a perspective view photomicrograph enlarged approximately 175 times of a backing web of the pressure-sensitive adhesive fastener of the present invention having a 100×100 mesh pattern.
Figure 3A:
FIG. 3a is a perspective view photomicrograph enlarged approximately 90.5 times of a pressure-sensitive adhesive fastener comprising a backing web similar to that shown in FIG. 3.

As shown in FIG. 2, the maximum internal cross-sectional area of the thinned membrane end portion 36 comprising each microbubble 38 (as measured in plane $X_2$ in FIG. 2), is greater than the minimum internal cross-sectional area (as measured in plane $X_1$ in FIG. 2), of the relatively thicker base portion 34 of the bulbous surface aberration 26 from which the microbubble 38 originates. These measurements are made in a pair of parallel planes oriented perpendicular to the amplitude or axis of the bulbous surface aberration 26 (as represented by "Y" in FIG. 2) with the microbubble 38 in its fully expanded condition. This produces a bulbous surface aberration 26 having a mushroom-like appearance or shape when viewed from a side elevation. A particularly preferred microbubbled web for use as the backing web 24 of the present invention is described in U.S. Pat. No. 4,846,821, entitled "Substantially Fluid-Impervious Microbubbled Polymeric Web Exhibiting Low Levels Of Noise When Subjected To Movement", which issued to Julie W. Lyons, Charles F. Battrell, William R. Ouellette, and John J. Curro on Jul. 11, 1989, and which patent is incorporated herein by reference.

A unique feature of the backing webs 24 of the present invention having a microbubbled end portion 36 is the thinning of the walls as one proceeds upward from the base to the side walls to the top of the bulbous surface aberration 26. This apparent wall thinning reduction from the base to the top of the structure is approximately 10:1. While not wishing to be bound by theory, it is believed the thinning of the walls is due primarily to the plastic yielding which takes place in the microbubbled end portion 36 of the bulbous surface aberration 26 relative to the more elastic deformation which takes place in the base portion 34 of the bulbous surface aberration 26. Once plastic deformation in the end portion 36 has occurred, there is little, if any, tendency towards elastic recovery, i.e., shrinking of the microbubbled end portion 36 of the bulbous surface aberration 26. By way of contrast, there is relatively less plastic deformation occurring in the base portion 34 of the bulbous surface aberration 26. Accordingly, once the forces causing deformation of the base portion 34 are removed, the base portion 34 undergoes at least a degree of elastic recovery while the plastically deformed microbubbled end portion 36 joined thereto does not. As a result, the minimum internal cross-sectional area of the thicker base portion 34 of the bulbous surface aberration 26, as measured in a plane approximately coinciding with the point at which the base portion 34 is joined to the microbubbled end portion of this bulbous surface aberration 26 (e.g., plane $X_1$ in FIG. 2), is typically smaller than the maximum internal cross-sectional area of the fully expanded microbubbled end portion 36, as measured in a parallel plane (e.g., plane $X_2$ in FIG. 2) located along the amplitude or axis of the bulbous surface aberration 26. Thus, the bulbous surface aberrations 26 of the present invention normally exhibit a mushroom-like cross-sectional appearance or shape when viewed from a side elevation.

The degree of thinning in the microbubbled end portion 36 of the backing web 24 of the present invention is sufficient to substantially remove the stiffness from the end portion 36 of the bulbous surface aberration 26, effectively converting it to a thin, compliant, easily deformable (highly flexible) membrane. In the event the web of starting material is opaque, the degree of thinning is normally sufficient to render the microbubbled end portion 36 of the bulbous surface aberration 26 substantially transparent. While not wishing to be bound by theory, it is believed that removing the stiffness from the microbubbled end portion 36 of each bulbous surface aberration 26 provides a multiplicity of hinges or flex points throughout the backing web 24. As a result, backing webs 24 having microbubbled bulbous surface aberrations 26 according to the present invention are substantially less stiff than other backing webs 24. This decreased stiffness is important in order to allow the bulbous surface aberrations 26 of the resultant pressure-sensitive adhesive fastener 20 to comply and conform with the contacting surface of the landing member to which the fastener is attached thereby providing the desired shear and peel properties of the pressure-sensitive adhesive fastener 20.

Because of the extremely thin membrane-like behavior of the microbubbled end portion 36 of the bulbous surface aberration 26, it may be necessary to subject the backing web samples to be evaluated to a slight fluid pressure to fully expand the microbubbled end portion 36 of the bulbous surface aberration 26 prior to determining if the aforementioned cross-sectional area relationship is present in any given backing web sample. A relatively low pneumatic pressure applied to the second surface 32 of the backing web 24 will in most instances suffice.

A particularly preferred method for analyzing the cross-section of the bulbous surface aberration 26 involves casting samples of the backing web 24 while it is in its fully expanded condition, and thereafter photographing, on a highly enlarged scale, very thin cross-sectional slices taken from the casting. This procedure is described in detail in the above-referenced U.S. Pat. No. 4,846,821 issued to Lyons et al. on Jul. 11, 1989. It must, of course, be recognized that it will in some instances be possible to produce sliced web samples of the present invention wherein the microbubbled end portion 36 of a given bulbous surface aberration 26 may not exhibit a mushroom shaped cross-section when viewed from a particular side elevation. This may, in fact, be due to where the section is taken through the particular bulbous surface aberration 26 rather than a failure of the bulbous surface aberration 26 to satisfy the cross-sectional area relationship described earlier herein, i.e., the same bulbous surface aberration 26, if sectioned along a different axis, may indeed exhibit a mushroom-like cross-section. Therefore, any analysis taken to determine if a mushroom-like cross-section exists in the vast majority of bulbous surface aberrations 26 present in any given backing web sample should simultaneously examine a multiplicity of bulbous surface aberrations 26 rather than an isolated bulbous surface aberration 26.

The number of bulbous surface aberrations per square inch on the backing web 24 can vary by approximately three orders of magnitude. It should be noted that as the number of bulbous surface aberrations per square inch increases, the size of the bulbous surface aberrations 26 necessarily decreases. An example of the size range of the bulbous surface aberrations 26 is shown in the following table:

| Textured Film Pattern | # Structures per square inch | Structure Height | Structure Width |
|---|---|---|---|
| 100 square | 10,000 | ~7 mil | ~8 mil |
| 60 square | 3,600 | ~10 mil | ~11 mil |
| 20 square | 400 | ~15 mil | ~16 mil |
| 60 Twill | 3,600 | ~12 mil | ~13 mil |

A backing web 24 having greater than about 62,500 bulbous surface aberrations per square inch (about 2 to about 3 mil height and width) represents the upper limit on the number of bulbous surface aberrations per square inch (a lower limit upon the size of the aberrations). At this relatively large number of structures per square inch and small size of each bulbous surface aberration 261 there is an impact on the adhesion properties of the pressure-sensitive adhesive fastener 20. The bulbous surface aberrations 26 become so small that the coating of even a small amount of pressure-sensitive adhesive onto them would make a smooth continuous fastening surface rather than a textured fastening surface 22 as required in the present invention. The result would be a loss of the adhesion benefits of having a pressure-sensitive adhesive fastener 20 having a textured fastening surface 22.

The lower limit on the number of bulbous surface aberrations per square inch is about 20 bulbous surface aberrations per square inch. Larger bulbous surface aberrations do not have sufficient strength to keep the microbubble 38 "inflated" during use of the pressure-sensitive adhesive fastener 20. The strength of the microbubbled end portion 36 is related to the critical buckling load for each microbubble 38. The critical buckling loading is an applied force that causes the microbubble 38 to permanently deform into a new structure. The mathematical theory has been presented by G. Meneges & F. Knipschild for plastics (*Mechanics of Cellular Plastics*, Ed. N. C. Hilyard, McMillan Publishing, New York (1982)). Generally, the larger the microbubble structure, the less force is required to buckle the microbubble 38. With all other factors being nearly equal, such as wall thickness and modulus, then the radius of the microbubble 38 and the volume fraction of the microbubble 38 become the important variables affecting critical buckling load. The volume fraction (ratio of material to cell size of the cell) decreases as the microbubble size increases. The radius of the microbubble 38 varies linearly with critical buckling force, whereas the volume fraction varies by the square power. Thus, a decrease in the volume fraction correlates to a squared lowering of the force required to buckle the microbubble 38. There are several methods to reduce the incident of buckling in larger microbubbles, such as reducing the nip roll pressures encountered during use or lowering the rewind tension. However, at some point, the large size of the microbubble 38 will lower the critical buckling force such that it is unrealistic to be able to generate a non-buckling bulbous surface aberration 26. A backing web 24 having about 20 bulbous surface aberrations per square inch, more practically about 100 bulbous surface aberrations per square inch (diameters and heights of about 20 to about 30 mil) represents the lower limit on the number of structures per square inch (upper limit on the size of each structure).

The number of bulbous surface aberrations per square inch is preferably in the range of about 400 to about 10,000 bulbous surface aberrations per square inch, most preferably from about 1,000 to about 5,000 bulbous surface aberrations per square inch, as measured in an area which contains the bulbous surface aberrations 26. It should be noted, however, that the entire first surface 30 of the backing web 24 need not contain bulbous surface aberrations 26. Bulbous surface aberrations 26 may be employed only on those portions of the first surface 30 of the backing web 24 which are intended to perform a fastening function while other portions of the first surface 30 need not contain such bulbous surface aberrations 26 so that these portions of the first surface 30 may serve additional or other functions in certain predetermined locations.

Further, the bulbous surface aberrations 26 employed on the backing webs 24 need not all be of the same size or form a regular or repeating pattern. The pattern, size, and spacing of the bulbous surface aberrations 26 may be uniform or non-uniform as desired. For example, the bulbous surface aberrations 26 may be of dissimilar sizes to vary the fastening capability of certain portions of the fastener. In a preferred embodiment of the present invention, the bulbous surface aberrations 26 have the same size and are formed on the backing web 24 in a regular repeating pattern.

The microbubbled end portion 36 of the present invention is preferably a continuous membrane (it has a continuous surface) so as to maintain the flexibility of the bulbous surface aberrations 26. The term "continuous" is used herein to mean that the surface or membrane of the end portion 36 is uninterrupted by structures formed into the end portion 36. For example, the microbubbles 38 may rupture to form a volcanic type structure (an aperture in the end portion 36). A non-continuous end portion having an aperture would have a very low critical buckling load. Thus, when a layer of pressure-sensitive adhesive is coated onto the apertured end portion, the adhesive would buckle the structure and could self-adhere and help to set the buckled structure into a non-flexible structure. This loss of flexibility in the structure negatively impacts on the peel and shear properties of the resultant fastener. Thus, the surface of the end portion 36 is preferably continuous.

The backing web 24 of the present invention is also preferably substantially impervious to adhesive so that adhesive applied to the backing web 24 does not penetrate through the material forming the backing web 24 and contact other portions of the backing web 24 or machinery forming the backing web 24.

In general, it has been found that preferred starting materials to be used as the incoming film for producing the backing webs 24 of the present invention are polymeric film materials (polymeric webs). Preferred plastic resin families for use as the backing web 24 are polyolefins and thermoplastic elastomers. The polymers can be used singularly or blended with other polymer resins. Examples of polyolefins for use herein as the backing web 24 include linear polyethylene, both low density (LLDPE) and medium density (LMDPE); ethylene-vinyl acetate copolymer (EVA); ethylene-methyl acrylate copolymer (EMAC); ethylene-ethyl acrylate copolymer (EEA); ultralow-density polyethylene (ULDPE); and polypropylene random ethylene copolymers. Examples of suitable thermoplastic elastomers include polyester/polyether block polymers, polyamide/polyether block polymers; and ionomer metal salts of ethylene/methacrylic acid copolymers. Preferred materials exhibit a low degree of molecular orientation, and most preferably exhibit low-yield and high-elongation characteristics. In addition, the starting films preferably strain harden. Exemplary of preferred starting films are materials such as linear low-density polyethylene, blends of linear low-density polyethylene and low-density polyethylene, as available from Ethyl VisQueen of Richmond, Va.; linear very-low-density polyethylene as available from TUREX, Inc. of Harrisville, R.I.; and block co-polymers such as polyester-polyether, which are designated as Hytrel, as available from E. I. DuPont Nemours & Co. of Wilmington, Del.

The bulbous surface aberrations 26 and thus, generally, the backing web 24 should be wettable by pressure-sensitive adhesives. If the surface of the backing web 24 is wettable by pressure-sensitive adhesives, then the adhesive will easily spread over the first surface 30 of the backing web 24, especially the bulbous surface aberrations 26, such that a uniform or even coating of adhesive is positioned on the bulbous surface aberrations 26 and/or the backing web 24. For water-based pressure-sensitive adhesives, the surface of most polymeric films can be corona treated to improve the wetting out of the adhesive. Also, the corona treatment improves the bonding of the pressure-sensitive adhesive to the surface of the backing web 24. This is important because the fastening system needs to fail at the landing member/pressure-sensitive adhesive interface during use rather than between the interface between the backing web and the pressure-sensitive adhesive. Corona treatment of polymeric films to enhance the wettability and surface adhesion of materials is discussed in U.S. Pat. No. 3,703,569 entitled "Corona Treatment Of Antistat Containing Sheet Of Ethylene or Ethylene Copolymer" which issued to R. I. Wolkowicz on Nov. 21, 1972; U.S. Pat. No. 4,029,876 entitled "Heat-Treated, Corona Treated Polymer Bodies And A Process For Producing Them" which issued to Theodore R. Beatty et al. on Jun. 14, 1977; U.S. Pat. No. 4,351,784 entitled "Corona Treatment Of Perforated Film" which issued to Paul E. Thomas et al. on Sep. 28, 1982; and U.S. Pat. No. 4,535,020 entitled "Perforated Film" which issued to Paul E. Thomas et al. on Aug. 13, 1985. Each of these patents are incorporated herein by reference.

The backing web 24 of the present invention can be manufactured using a number of different methods and procedures. Particularly preferred methods and apparatus for producing microbubbled backing webs 24 of the present invention are described in U.S. Pat. No. 4,772,444, entitled "Method And Apparatus For Making Microbubbled And/Or Microapertured Polymeric Webs Using Hydraulic Pressure", which issued to John J. Curro, Charles W. Chappell, and James W. Cree, on Sep. 20, 1988, which patent is incorporated herein by reference. An exemplary method for producing the microbubbled backing webs 24 of the present invention is described in the above patent and involves the use of a high-pressure liquid stream. A microbubbled backing web 24 of the present invention was made in accordance with a high-pressure stream liquid process using a laminate structure. The starting material comprised a web which is a blend of polyethylenes, designated Ethyl VisQueen No. XP-4337, as is available from Ethyl VisQueen of Richmond, Va. The initial thickness of the web prior to processing was nominally 1.2 mils (0.0012 in). The apertured sheet portion of the forming structure was constructed of laminar layers of thin metal, each having circular holes measuring approximately 8 mils (0.008 inches) in diameter. The hole pattern was regularly spaced and exhibited a density of 100 holes per linear inch by 100 holes per lineal inch. The overall thickness of the apertured lamina sheet portion of the forming structure measured approximately six mils (0.006 in). Immediately beneath the laminar apertured sheet portion of the forming structure there was provided a woven wire porous backup layer or screen comprised of filaments having a diameter of approximately 1 mil (0.001 in) arranged in a twilled Dutch weave pattern (there is a degree of filament overlap with this pattern), the screen having a filament density of approximately 325 filaments per lineal inch by approximately 2,300 filaments per lineal inch, as available from the Facet Co. of Greensboro, N.C. The laminar apertured sheet portion and the porous backup layer were bonded to one another by diffusion bonding, as performed by the Facet Co., to form an integral forming cylinder which was mechanically supported at its innermost surface without "blinding" the porosity of the innermost screen. The cylindrical forming structure rotated about a stationary drum having a centrally located vacuum chamber.

The web was fed onto the aforementioned rotating forming structure at a speed of approximately 300 feet per minute and subjected to a high pressure water jet operating at a gauge pressure of approximately 800 pounds per square inch and a water flow rate of approximately 3 gallons per minute per cross-machine direction of web width. The temperature of the water in the high pressure water jet was approximately 180° F., as measured at the nozzles.

Cooling water at a temperature of approximately 50° F. was applied at a rate of approximately 1 gallon per minute per cross-machine direction inch of web width.

A vacuum chamber was maintained at approximately 7.5 inches of Mercury to provide screen cooling and chamber venting.

The resultant microbubbled backing web 24 exhibited a regularly repeating pattern of bulbous surface aberrations 26, each having a highly thinned, mushroom-shaped membrane coincident with its point of maximum amplitude. The density of the bulbous surface aberrations 26 corresponded to the density of the apertures in the laminar apertured sheet portion of the forming structure, i.e., approximately 100 bulbous surface aberrations per lineal inch by approximately 100 bulbous surface aberrations per lineal inch. The overall caliper of the resultant backing web 24 was approximately 6 mils (0.006 in), as measured under a low load condition of approximately 0.21 pounds/in$^2$ (95 grams/in$^2$). The microbubbled end portions 36 of the bulbous surface aberrations 26 of the opaque web were substantially transparent.

The second surface 32 of the backing web 24 may be laminated to one or more additional webs to provide increased strength for the pressure-sensitive adhesive fastener 20. The second web may be manufactured from a wide variety of materials commonly used for backings of fasteners. The second web preferably comprises a generally flexible material so as to provide higher peel resistance for the fastener. The backing web 24 may be laminated to the other webs by any of the several lamination techniques as is known in the art. For example, the backing web 24 may be laminated by wet, extrusion, dry, thermoplastic and pressure processes.

When the backing web 24 is laminated to another web(s), several operating requirements need to be maintained during the lamination process so the bulbous surface aberrations 26 are not altered or changed. The nip roll pressures of the equipment should be maintained below the critical buckling load of the particular bulbous surface aberrations 26. If the laminating processes require heating to dry or activate certain curing agents, then the temperature of the backing web 24 must be maintained below the softening point of the material forming the backing web 24. The laminated bond strength must be greater than o the peel and shear adhesion forces of the resultant fastener so that the bond between the fastener and the landing member fails before the bond between the backing web and the laminated second web.

The second component of the pressure-sensitive adhesive fastener 20 of the present invention is a layer of adhesive coated over and bonded to at least a portion of the surface of the bulbous surface aberrations 26. Adhesives useful in the present invention are pressure-sensitive adhesives formulated to adhere to a surface at ambient temperature by briefly applying light pressure alone. Pressure-sensitive adhesives that work in the present invention are categorized into emulsion, solvent, and hot melt pressure-sensitive adhesives.

Emulsion pressure-sensitive adhesives include a wide variety of polymeric materials (usually thermoplastic or elastomerics) dispersed in a continuous aqueous phase. The amount of water in the formulation varies but usually contains around 50% of water by weight. The emulsion pressure-sensitive adhesives may be applied to the backing web 24 by a variety of coating processes. The removal of water by evaporation is usually aided. As the water is being removed, the dispersed particles begin to aggregate into a gel-like mass. After continued removal of the water, the gel-like mass coalesces into a continuous film.

The solvent pressure-sensitive adhesives consist of thermoplastic or elastomeric compositions dissolved in an appropriate aqueous or organic solvent at levels from 1% to 99% solids. All polymer systems in this class are in solutions in the solvent and are not to be confused with emulsions, where the polymer is actually in dispersions. Solvent pressure-sensitive adhesives may be applied to the backing web by coating processes which are very similar to emulsion processes. The removal of solvent can be aided by thermal, vacuum, or forced air procedures. Thus, removal of the solvent from the pressure-sensitive adhesive leaves a solid film of adhesive.

Hot melt pressure-sensitive adhesives consist of compositions that are capable of being melted and applied to a substrate in its molten state which then cool and solidify relatively quickly. Examples of suitable hot melt adhesives are ethylene-vinyl acetate (EVA) or rubber-based hot melt pressure-sensitive adhesives. A particularly preferred hot melt pressure-sensitive adhesive is a Kraton based adhesive with tactifiers and other additives such as the material marketed by Findley Adhesives, Inc. of Elm Grove, Wis., under the tradename Findley 990 or H-2085.

Various polymeric raw materials may be used in the formulation of the pressure-sensitive adhesives useful in the present invention. Exemplary of polymers known in the art which may be used are natural rubber, polyisobutylene, polyvinyl ether, various types of synthetic rubber, ethylene copolymers, vinyl copolymers, and polyurethanes. The preferred pressure-sensitive adhesives for use in the present invention are emulsion pressure-sensitive adhesives. However, solvent-based pressure-sensitive adhesives or hot melt pressure-sensitive adhesives can be applied. Most of the above-mentioned pressure-sensitive adhesives which can be used in the present invention are disclosed in the *Handbook of Adhesives* at pages 535-539 and 726-728, which are herein incorporated by reference.

The layer of pressure-sensitive adhesive 28 need be coated on only a portion of the surface of the bulbous surface aberrations 26. Typically, at least the surface of the end portion 36 of each of the bulbous surface aberrations 26 is coated with the adhesive. It is desirable that the adhesive be coated on at least the surface of the bulbous surface aberrations 26 (both the end portion 36 and the base portion 34). While it is envisioned that the pressure-sensitive adhesive could be coated over just the land portions 39 of the first surface 30 of the backing web (the land portions 39 being the surface between the bulbous surface aberrations 36), it has been found that it is preferable to coat at least a portion of the surface of the bulbous surface aberrations. Due to the high speed of and coating techniques used in the manufacturing processes used to produce the pressure-sensitive adhesive fasteners of the present invention, the pressure-sensitive adhesive is typically coated over the first surface 30 of the backing web 24 (i.e., all of the surface of the bulbous surface aberrations 26 and the land portions 39 of the first surface 30 are coated). As shown in FIG. 2, it is desirable that the pressure-sensitive adhesive is uniformly coated over and bonded to the first surface 30 of the backing web 24 to form a continuous thin layer of adhesive. However, to reduce the amount of adhesive used in making the fastener, only a portion, preferably the microbubbled end portion 36, of the backing web 24, only need be coated with adhesive.

In addition, the layer of pressure-sensitive adhesive 28 need not be coated on each bulbous surface aberration 26 or the entire first surface 30 of the backing web 24. (i.e., the area coverage of the adhesive may vary depending upon the circumstances of use of the fastener.) For example, certain zones or areas of the backing web 24 may not be coated with adhesive since an adhesive property may not be desired in these particular zones or areas. (i.e., partial area coverage of adhesive) The pattern of the area coverage of the adhesive may thus widely vary depending upon the circumstances of the use of the fastener 20. Preferably, adhesive is coated over the entire first surface 30 of the backing web 24 such that there is complete area coverage of the first surface 30 with a layer of adhesive 28.

The coat weight of the pressure-sensitive adhesive on the backing web 24 has significant impact on the adhesion properties of the resultant pressure-sensitive adhesive fastener 20. An excess amount of pressure-sensitive adhesive coated onto the bulbous surface aberrations 26 results in a loss of adhesion benefits since the voids between the bulbous surface aberrations 26 could be completely filled with pressure-sensitive adhesive such that a smooth continuous fastening surface would be produced. Thus, in order to maintain a textured fastening surface 22 for the fastener of the present invention, the coat weight of the pressure-sensitive adhesive should be great enough to cover the first surface 30 of the backing web 24 but not so much as to completely fill the void spaces between the bulbous surface aberrations 26. It has been found that a pressure-sensitive adhesive coat weight between about 0.002 g/in$^2$ to about 0.08 g/in$^2$ is desirable for the fasteners of the present invention. More specifically, for example, for typical water-based emulsion pressure-sensitive adhesives applied using a mayer rod applicator, the typical coat weight for a 5 bar mayer rod applicator is about 0.0201 g/in$^2$; for a 10 bar mayer rod applicator the typical coat weight is about 0.0210 g/in$^2$; and for a 20 bar mayer rod applicator the typical coat weight is about 0.0248 g/in$^2$. It has also been found that much less hot melt adhesive may be used in order to effectively form the fastener of the present invention. For example, for a 5 bar mayer rod applicator, the typical coat weight of hot melt pressure-sensitive adhesive is about 0.0032 g/in$^2$; for a 10 bar mayer rod - the typical coat weight is about 0.0041 g/in$^2$; and for a 20 bar mayer rod - the typical coat weight is about 0.0549 g/in$^2$.

Whether or not repeated pressure-sensitive adhesive coatings have been made onto the backing web 24 also has significant impact on the adhesion properties of the resultant pressure-sensitive adhesive fastener 20. Repeat coating of the pressure-sensitive adhesive onto the backing web 24 introduces a structure factor to the surface of the fastener. The pressure-sensitive adhesive bridges the gap from the top of one bulbous surface aberration 26 to another. This phenomenon provides an adhesion benefit of increasing the level of fast grab for the substrate. For pressure-sensitive adhesive systems, fast grab is defined as sufficient/adequate bond security under low load applications. One must balance the benefit of the fast grab provided by the bridging of the pressure-sensitive adhesive with the danger that repeat coatings of adhesive may fill the void between the bulbous surface aberrations 26. Thus, the above-defined coat weights have been found desirable in providing the maximum benefit for the fasteners of the present invention.

Several methods for coating and bonding pressure-sensitive adhesives onto the backing web 24 may be used to apply the pressure-sensitive adhesive to the backing web 24. For example, excess coating techniques may be applied to coat the pressure-sensitive adhesive onto the backing web 24. An unmetered or partially metered volume of pressure-sensitive adhesive is applied onto the backing web 24. A post-coating metering system removes the excess coating via a knife, blade, rod, and/or a dip coater as are known in the art. Another technique is to pre-meter coat the pressure-sensitive adhesive onto the backing web 24. A predetermined volume of pressure-sensitive adhesive is applied onto the backing web 24. Post-metering is not required since the applied volume has been accurately controlled via, for example, rotogravure, offset gravure, kiss roll pressure, reverse roll, spray curtain, cast and/or orifice coaters as are known in the art. Further, a hybrid coating technique may be used to coat the pressure-sensitive adhesive onto the backing web 24. This technique would combine the excess and pre-metered coating principals. For example, the pressure-sensitive adhesive may be kiss coated via air blade doctoring onto the backing web 24 and post-metered with roll pressure with a finishing bar to obtain the same results. An excellent review of the details of each of the above techniques can be found in *Coating and Laminating Machines*, H. B. Weiss, Converting Technology Company, Milwaukee, Wis. (1977), incorporated herein by reference.

Figure 9:
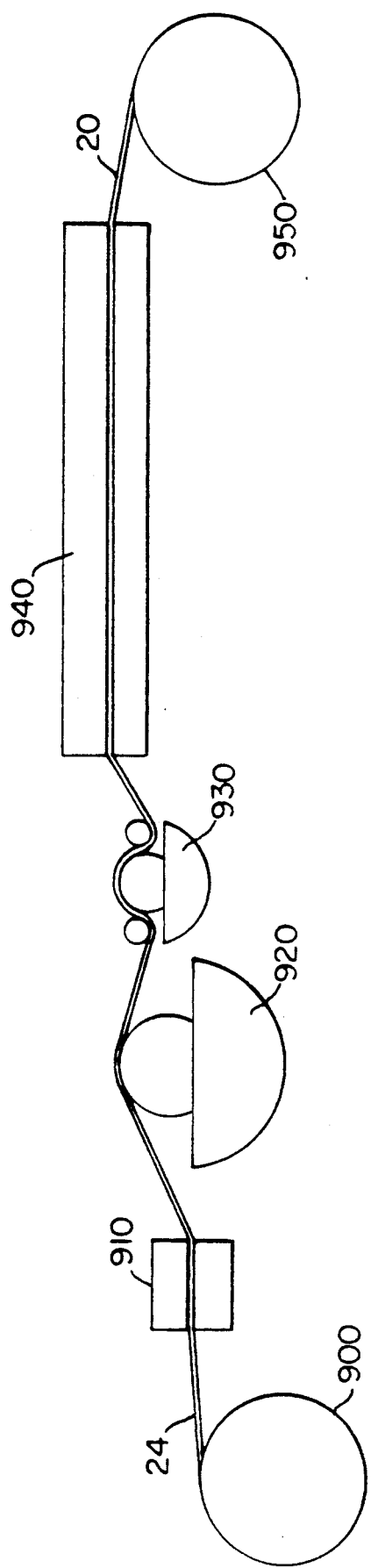
FIG. 9 is a side view of an apparatus and method for making the pressure-sensitive adhesive fastener of the present invention.

An exemplary method of making the pressure-sensitive adhesive fastener 20 in accordance with the present invention is illustrated in FIG. 9. As shown in FIG. 9, after the bulbous surface aberrations 26 have been formed on the backing web 24, the backing web 24 is fed (about 20 to about 40 feet per minute) from an unwind roll 900 to a corona treatment apparatus 910 wherein the backing web 24 is corona treated to allow for more uniform dispersion of adhesive over the first surface 30 of the backing web 24, especially over the bulbous surface aberrations 26. The backing web is then passed over a single roll Kiss Coater 920 where an unmetered or partially metered amount of water-based emulsion pressure-sensitive adhesive is applied. The coated backing web 24 is then passed over a Mayer rod 930 for metering the final cast weight of adhesive onto the backing web. The composite material is then passed into an infrared dryer 940 (37.5 kilowatt/440 volt) which preferably operates at ⅓ power with an air exhaust temperature of 100° F. for a period of time of 10 to 30 seconds to bond the adhesive to the backing web. The resultant pressure-sensitive adhesive fastener 20 is then taken up by a wind-up roll 950.

A coating process objective should be to minimize the deformation of the coated bulbous surface aberrations 26. Elevated temperatures, excessive metering pressure or elevated rewind roll tension can and will permanently deform the coated surface of the bulbous surface aberrations 26 on the backing web 24. Thus, certain temperatures, pressures and tensions should be avoided. These may be determined according to the particular backing web 24 used in the process.

Figure 4:
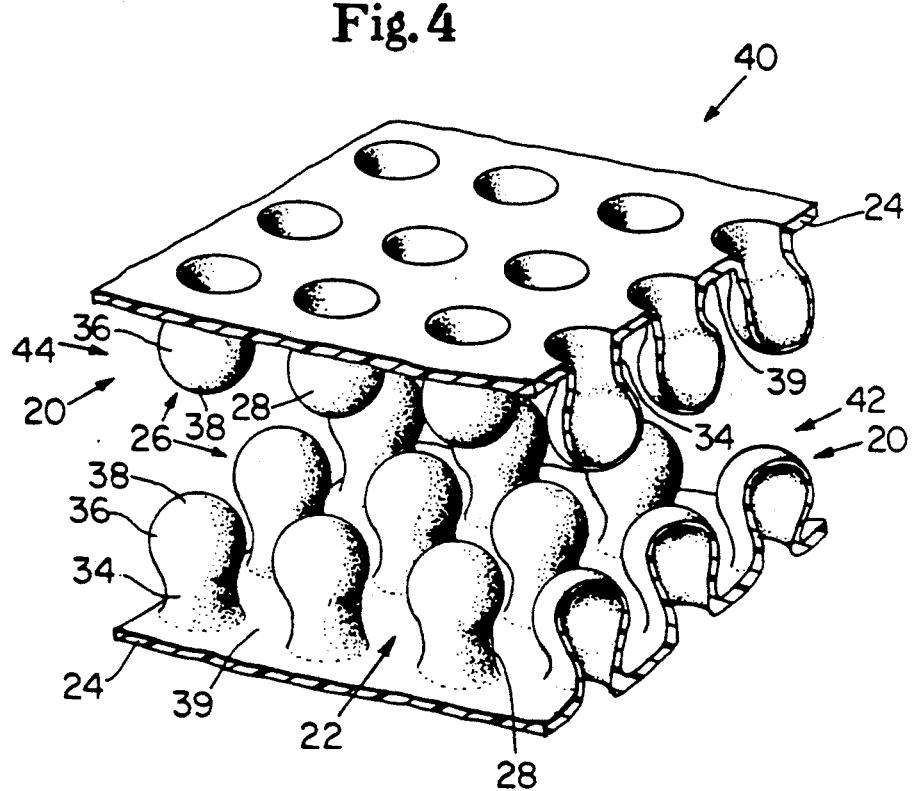
FIG. 4 is a partially cut-away perspective view of a fastening system of the present invention comprising a first member comprising the pressure-sensitive adhesive fastener of the present invention and a landing member comprising the pressure-sensitive adhesive fastener of the present invention.

The present invention also relates to a fastening system for securing two articles to each other that utilizes the pressure-sensitive adhesive fastener 20 of the present invention. As shown in FIG. 4, the fastening system 40 preferably comprises a first member 42 comprising the pressure-sensitive adhesive fastener 20 as previously described herein and a landing member 44 engageable with the pressure-sensitive adhesive fastener 20.

The landing member 44 is the body or material in which the first member 42, the pressure-sensitive adhesive fastener 20 of the present invention, comes into contact during use. (i.e., the adherend). The benefits of the shear and peel properties of the pressure-sensitive adhesive fastener 20 of the present invention is particularly achieved when the landing member 44 has a textured contacting surface 46. ("Textured" is used herein to mean surfaces that have surface projections.) Without wishing to be bound by any theory, a landing member 44 having a textured contacting surface 46 is more effective because the bulbous surface aberrations 26 of the pressure-sensitive adhesive fastener 20 mechanically interfere with the projections on the textured contacting surface 46 of the landing member 44 to increase the shear force resistance while the peel force resistance is enhanced because a greater amount of surface area between the two components is adhesively in contact. Conversely, as the contacting surface 46 of the landing member 44 becomes flatter or smoother, the shear force resistance decreases and the peel force is reduced to near zero because the bulbous surface aberrations 26 are not interfering with the projections on the contacting surface 46 of the landing member 44 and less, if almost insignificant, surface area is adhesively in contact. Thus, the texturing of the contacting surface 46 of the landing member 44 has a large degree of control on the final properties of the fastening system 40.

The landing member 44 may comprise a large variety of materials having textured contacting surfaces 46 including nonwoven webs, polymeric films, woven webs, cloths with weaving in the surfaces or knitting, skin, a backing web having bulbous surface aberrations 26 of the type hereinbefore described, or another pressure-sensitive adhesive fastener of the present invention.

To fasten two objects together, the textured fastening surface 22 of the pressure-sensitive adhesive fastener 20 of the present invention is contacted to the textured contacting surface 46 of the landing member 44 and slight pressure is applied to one or both of the members to adhere the two objects together.

Fastening systems of the present invention have been found to be particularly useful and beneficial when applied to disposable absorbent articles. As used herein, the term "disposable absorbent article" refers to articles which absorb and contain body exudates and, more specifically, refers to articles which are placed against or in proximity to the body of the wearer to absorb and contain the various exudates discharged from the body and which are intended to be discarded after a single use (i.e., they are not intended to be laundered or otherwise restored or reused). Examples of suitable disposable absorbent articles include diapers, incontinent briefs and undergarments, sanitary napkins, bibs, bandages, and the like.

Figure 5:
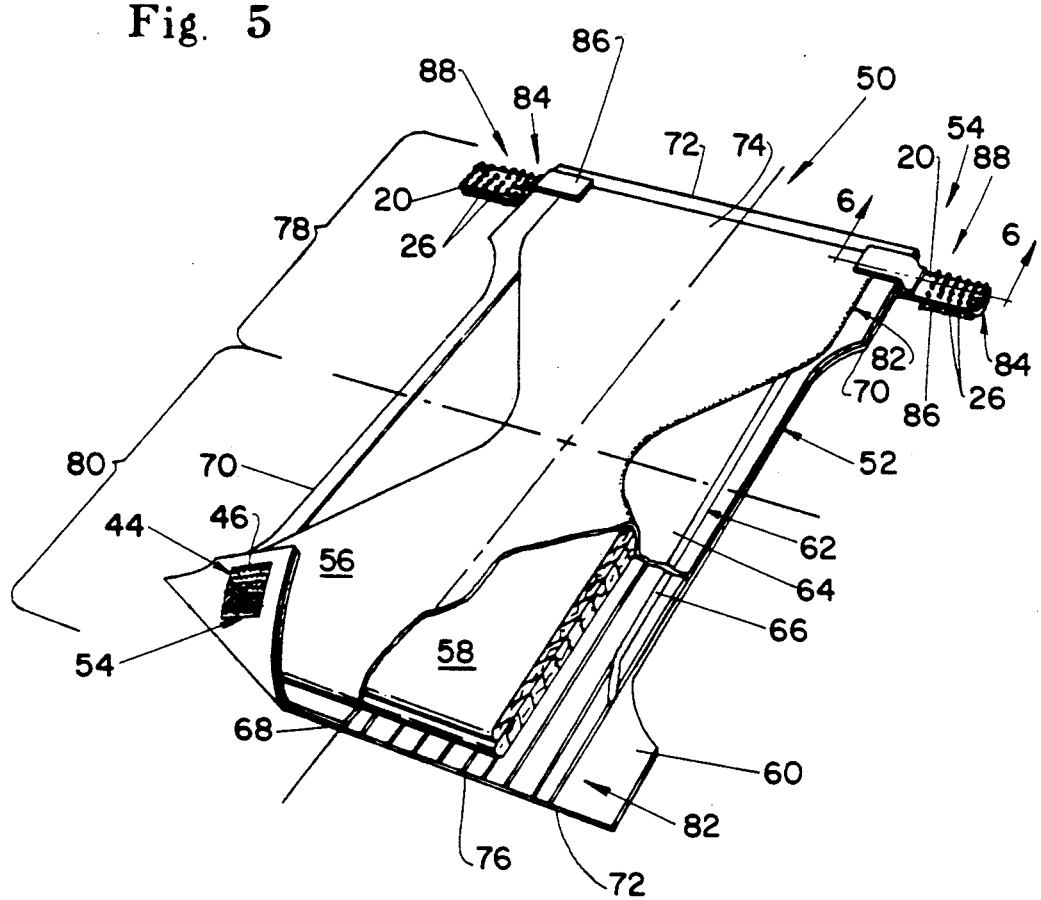
FIG. 5 is a partially cut-away perspective view of a diaper embodying the fastening system and the pressure-sensitive adhesive fastener of the present invention.

A preferred embodiment of a disposable absorbent article embodying the present invention is shown in FIG. 5 as a diaper 50. As used herein, the term "diaper" refers to a garment generally worn by infants or incontinent persons that is drawn up between the legs and fastened about the waist of the wearer. Examples of the kinds of diapers to which the present invention is very readily adapted are shown in U.S. Pat. No. Re. 26,151 entitled "Disposable Diaper" which reissued to Robert C. Duncan and Norma L. Baker on Jan. 31, 1967; in U.S. Pat. No. 3,860,003 entitled "Contractable Side Portions For Disposable Diaper" which issued to Kenneth B Buell on Jan. 14, 1975; and in U.S. Pat. No. 4,834,735 entitled "High Density Absorbent Members Having Lower Density And Lower Basis Weight Acquisition Zones" which issued to Miguel Alemany and Charles J. Berg on May 30, 1989, which patents are incorporated herein by reference. It will be apparent from the following description that the fastening system illustrated and described herein may be applied to the body portion of such diapers. On the other hand, it will be understood the invention is not limited to any specific diaper structure or configuration.

FIG. 5 is a partially cut-away perspective view of a diaper 50 embodying the present invention prior to it being placed on the wearer by the diaper user. As can be seen in FIG. 5, a preferred diaper 50 comprises a body portion 52 and a fastening system 54.

A preferred body portion 52 comprises a liquid pervious topsheet 56, an absorbent core 58, a liquid impervious backsheet 60, and elastically contractible leg cuffs 62, each leg cuff preferably comprising a side flap 64 and one or more elastic members 66. While the topsheet 56, the absorbent core 58, the backsheet 60, the side flaps 64, and the elastic members 66 may be assembled in a variety of well known configurations, a preferred disposable diaper configuration is shown and described generally in the above-referenced U.S. Pat. No. 3,860,003 which issued to Kenneth B. Buell on Jan. 14, 1975, and which patent is incorporated herein by reference. In this preferred diaper configuration, the backsheet 60 is joined with the topsheet 56; the absorbent core 58 is positioned between the topsheet 56 and the backsheet 60; the side flap 64 extends outwardly from and along each side edge of the absorbent core 58; and the elastic member 66 is operatively associated with each side flap 64.

FIG. 5 shows a preferred embodiment of the body portion 52 in which the topsheet 56 and the backsheet 60 are coextensive and have length and width dimensions generally larger than those of the absorbent core 58. The topsheet 56 is superposed on the backsheet 60 thereby forming the periphery 68 of the body portion 52, in other words, the outer extent of the body portion 52. The periphery 68 comprises longitudinal edges 70 and end edges 72.

The body portion 52 has an inside surface 74 and an outside surface 76. In general, the outside surface 76 of the diaper 50 extends from one end edge 72 to the other end edge 72 of the diaper 50 and from one longitudinal edge 70 to the other longitudinal edge 70 of the diaper 50 and is the surface farthest from the wearer during use of the diaper 50. When a backsheet 60 is used, it typically forms the outside surface 76 of the body portion 52. The inside surface 74 is that surface of the diaper 50 opposite the outside surface 76 and in the embodiment shown is typically formed by the topsheet 56. In general, the inside surface 74 of the diaper 50 is that surface coextensive with the outside surface 76 and which is for the greater part in contact with the wearer when the diaper 50 is worn.

The diaper 50 has a first end region 78 and a second end region 80 extending from the end edges 72 of the diaper periphery 68 toward the lateral centerline of the diaper 50. Both the first end region 78 and the second end region 80 extend a distance of about one-half the length of the diaper 50 such that the end region comprise each half of the diaper 50.

Both the first end region 78 and the second end region 80 have panels 82. The panels 82 are those portions of the first end region 78 and the second end region 80 which overlap when the diaper 50 is fastened about the waist of the wearer. The extent to which the end regions overlap and thus the extent to which the panels 82 are formed, will depend on the overall dimensions and shape of the diaper 50 and the size of the wearer.

The diaper 50 is provided with a fastening system 54 for forming a side closure. Thus, the diaper 50 is fitted to the wearer and the panels 82 of the first end region 78 and the second end region BO are maintained in an overlapping configuration when the diaper 50 is worn.

In a preferred embodiment of the present invention as shown in FIG. 5, the fastening system 54 comprises a closure member 84 disposed adjacent each longitudinal edge 70 of the body portion 52 in the first end region 78, and a landing member 44 disposed on the outside surface 76 of the body portion 52 in the second end region 80. As shown in FIG. 5, the closure member 84 preferably comprises a tape tab 86 and the pressure-sensitive adhesive fastener 20 of the present invention (a first fastening element 88) while the landing member 44 preferably has a textured contacting surface 46 engageable with the first fastening element 88.

Each closure member 84 is intended to provide a fastening means for engaging the landing member 44 so as to provide a secure side closure for the diaper 50. Thus, the closure member 84 comprises at least the first fastening element 88. Each closure member 84 also preferably comprises a means for positioning the first fastening element 88 adjacent the landing member 44 so as to achieve a side closure. Thus, the closure member 84 may comprise any of the well known configurations and securement means for achieving a side closure on a diaper 50 such as an inner fastening member secured to the inside surface 74 and/or the outside surface 76 of the body portion 52, tape tabs, or belts. An exemplary embodiment of an inner fastening member is described in U.S. Pat. No. 4,699,622 entitled "Disposable Diaper Having An Improved Side Closure" issued to John W. Toussant and Margaret H. Hasse on Oct. 13, 1987, which patent is incorporated herein by reference. An embodiment of an incontinent undergarment using a belt suspension system is disclosed in U.S. Pat. No. 4,315,508 entitled "Self-Centering Multiple Use Garment Suspension System" issued to Bolick on Feb. 16, 1982, incorporated herein by reference.

As shown in FIG. 5, each closure member 84 most preferably comprises a tape tab 86. Any of the well known configurations and constructions of a tape tab 86 may be used. A preferred tape tab 86 is a Y-shaped tape tab as described in detail in U.S. Pat. No. 3,848,594 entitled "Tape Fastening System For Disposable Diaper" which issued to Kenneth B. Buell on Nov. 19, 1974 and which patent is incorporated herein by reference.

As shown in FIG. 5, a tape tab 86 is provided on both longitudinal edges 70 of the body portion 52, most preferably in the first end region 78.

Figure 6:
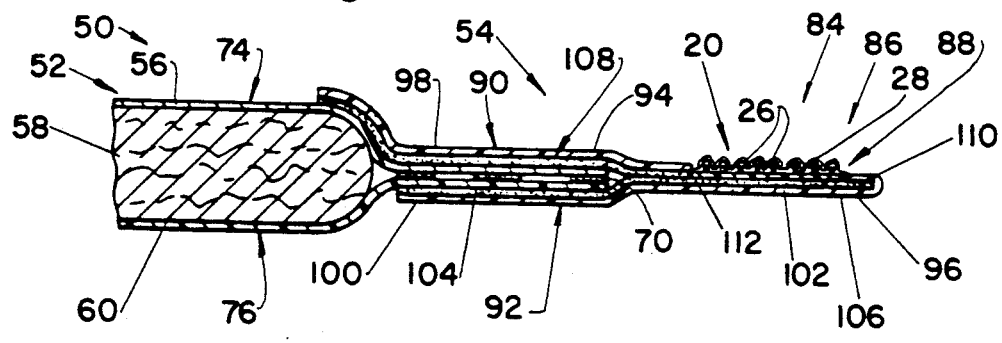
FIG. 6 is an enlarged fragmentary sectional view taken along line 6—6 of FIG. 5.

A particularly preferred tape tab 86 is illustrated in FIG. 6 and has a tab fastening surface 90 and a tab backing surface 92. The tab fastening surface 90 is that surface of the tape tab 86 designed to engage the landing member 44 of the present invention. Thus, the tab fastening surface 90 of the tape tab 86 will generally correspond to the inside surface 74 of the body portion 52. The tab backing surface 92 is that surface opposite of the tab fastening surface 90 and generally corresponds to the outside surface 76 of the body portion 52. The tab backing surface 92 is thus generally exposed during wear of the diaper 50.

The preferred tape tab 86 illustrated in FIG. 6 is one which is anchored to both the inside surface 74 and the outside surface 76 of the body portion 52 to create a fixed end 94 (i.e., that attachment of the tape tab 86 to the diaper 50 made during manufacture of the diaper 50). The tape tab 86 has another element which forms the tab end 96 (i.e., that joint made by the person in securing the diaper 50 to the wearer) that is secured to the fixed end 94 and extends beyond the longitudinal edge 70 of the body portion 52 so as to be secured to the landing member 44. Thus, the preferred tape tab 86 of the present invention has at least three elements, a first fixed portion 98, a second fixed portion 100, and a connective portion 102. The first fixed portion 98 is that portion of the tape tab 86 which is attached to the inside surface 74 of the body portion 52. The second fixed portion 100 is that portion of the tape tab 86 which is attached to the outside surface 76 of the body portion 52. The first fixed portion 98 and the second fixed portion 100 thus form the fixed end 94 of the tape tab 86. The connective portion 102 is that portion of the tape tab 86 which is attached to another portion of the diaper 50, generally the landing member 44, by the user when securing the diaper 50 on the wearer. The connective portion 102 thus forms the tab end 96. Additionally, the outer surface 104 of the second fixed portion 100 and the outer surface 106 of the connective portion 102 form the tab backing surface 92 of the tape tab 86 while the inner surface 108 of the first fixed portion 98 and the inner surface 110 of the connective portion 102 form the tab fastening surface 90 of the tape tab 86.

The preferred Y-shaped tape tab 86 of the present invention can be constructed in several ways. The first fixed portion 98, the second fixed portion 100, and the connective portion 102 can each be separate tapes which meet and are joined adjacent the longitudinal edge 70 of the body portion 52 in an area of joinder. A more practical structure for the tape tab 86 is one in which the connective portion 102 and either the first fixed portion 98 or the second fixed portion 100 are a unitary strip of tape material. If the connective portion 102 is unitary with the second fixed portion 100 as shown in FIG. 2, then the first fixed portion 98 is a separate element which is attached to the combined connective portion and the second fixed portion adjacent to the longitudinal edge 70 of the body portion 52.

Preferred materials for the tape tabs comprise a tape material such as tape code numbers XPF14.43.0, Y-9376, or Y-9030 available from The Minnesota Mining and Manufacturing Company, of St. Paul, Minn. The tape material in the embodiments are preferably a polyethylene film having a tab attachment means tailored to bond to the polyethylene positioned on the tape material. The tab attachment means may comprise any of those adhesives which provide an adequate bond with other portions of the diaper 50 and is preferably any of the pressure-sensitive adhesives well-known to those of ordinary skill in the art. Preferred tab attachment means is a pressure-sensitive adhesive such as Code Number XPF1.42.34 available from The Minnesota Mining and Manufacturing Company, of St. Paul, Minn.

The first fastening element 88 of the closure member 84 forms the closure between the closure member 84 and the landing member 44. Thus, the first fastening element 88 provides an element or elements that engage the textured contacting surface 46 of the landing member 44 to maintain the first end region 78 and the second end region 80 in an overlapping configuration to provide a secure side closure. The first fastening element 88 comprises the pressure-sensitive adhesive fastener 20 of the present invention.

The first fastening element 88 may be a separate member joined to and associated with the closure member 84 or a unitary member with the closure member 84. For example, the first fastening element 88 may be a discrete patch or strip of the pressure-sensitive adhesive fastener 20 of the present invention joined with the body portion 52 or the tape tab 86 (i.e., a separate member). Alternatively, the backing web 24 of the pressure-sensitive adhesive fastener 20 may be formed from the same element as an element of the closure member 84, e.g., the material for the connective portion of the tape tab 86 may comprise the backing web 24, such that the first fastening element 88 is a unitary member. Preferably, the first fastening element 88 is a separate strip of material joined to the fastening surface 90 of the tape tab 86.

The first fastening element 88 is preferably joined to either the body portion 52 or the tape tab 86. As used herein, the term "joined" encompasses configurations whereby the first fastening element 88 is releasably secured to the diaper 50 so the first fastening element 88 may be removed from the diaper 50 or its location during use and whereby the first fastening element 88 is affixed to the diaper 50 such that the first fastening element 88 is securely fastened to the diaper 50. Joined is also used to denote that the first fastening element 88 may be directly joined to the diaper 50 or may be indirectly joined to the diaper 50 such as by releasably securing or affixing the first fastening element 88 to an intermediate member which is in turn is releasably secured or affixed to the diaper 50. Preferably, as shown in FIG. 6, the first fastening element 88 is directly affixed to the connective portion of the tape tab 86 by a second tab attachment means 112.

In addition, the first fastening element 88 may be positioned anywhere on the diaper 50. When the closure member 84 comprises an inner fastening member, the first fastening element 88 is preferably positioned in the panels 82 of the first end region 78 adjacent the longitudinal edges 70. When the closure member 84 comprises a tape tab 86, the first fastening element 88 is preferably positioned either on all of or at least a portion of the fastening surface 90, or preferably on all of or at least a portion of the connective portion 102. Most preferably, the first fastening element 88 is disposed on the connective portion 102 on the fastening surface 90 of the tape tab 86

The landing member 44 of the fastening system 54 provides a means for securing itself and the closure member 84 together to provide a secure side closure and to maintain the first end region 78 and the second end region 80 in an overlapping configuration. The landing member 44 may be disposed anywhere on the diaper 50 so long as it engages the closure member 84 so as to provide the side closure. For example, the landing member 44 may be disposed on the outside surface 76 in the second end region 80, on the inside surface 74 in the first end region 78, or on any other portion of the diaper 50 which is disposed to engage the closure member 84. In addition, the landing member 44 may either be a discrete separate element affixed to an element of the diaper 50 (such as the topsheet 56 or the backsheet 60) or a unitary piece of material that is neither divided nor discontinuous with an element of the diaper 50 such as the topsheet 56 or the backsheet 60. While the landing member 44 can assume varying sizes and shapes, it preferably comprises one or more (at least one) separate patches of material secured to the body portion 52 to allow for a maximum fit adjustment at the waist of the wearer. The preferred embodiment of the diaper 50 illustrated in FIG. 5 has a rectangular-shaped landing member 44 secured to the outside surface 76 of the body portion 52 in the panels 82 of the second end region 80 adjacent each of the longitudinal edges 70.

In the embodiment shown in FIG. 5, the landing member 44 preferably comprises the same structure as the pressure-sensitive adhesive fastener 20 of the present invention so that the bulbous surface aberrations 26 on each member of the fastening system nest so as to provide a secure side closure.

In use, the diaper 50 is applied to the wearer by positioning the first end region 78 under the wearer s back and drawing the remainder of the diaper 50 between the legs of the wearer so the second end region 80 is positioned across the front of the wearer. The connective portion 102 of the tape tabs 86 are then positioned adjacent to the landing member 44 positioned on the outside surface 76 of the second end region 80 so the textured fastening surface 22 of the pressure-sensitive adhesive fastener 20 of the first fastening element 88 which is disposed on the fastening surface 90 of the tape tab 86 will engage the textured contacting surface 46 of the landing member 44 to form a side closure.

Figure 7:
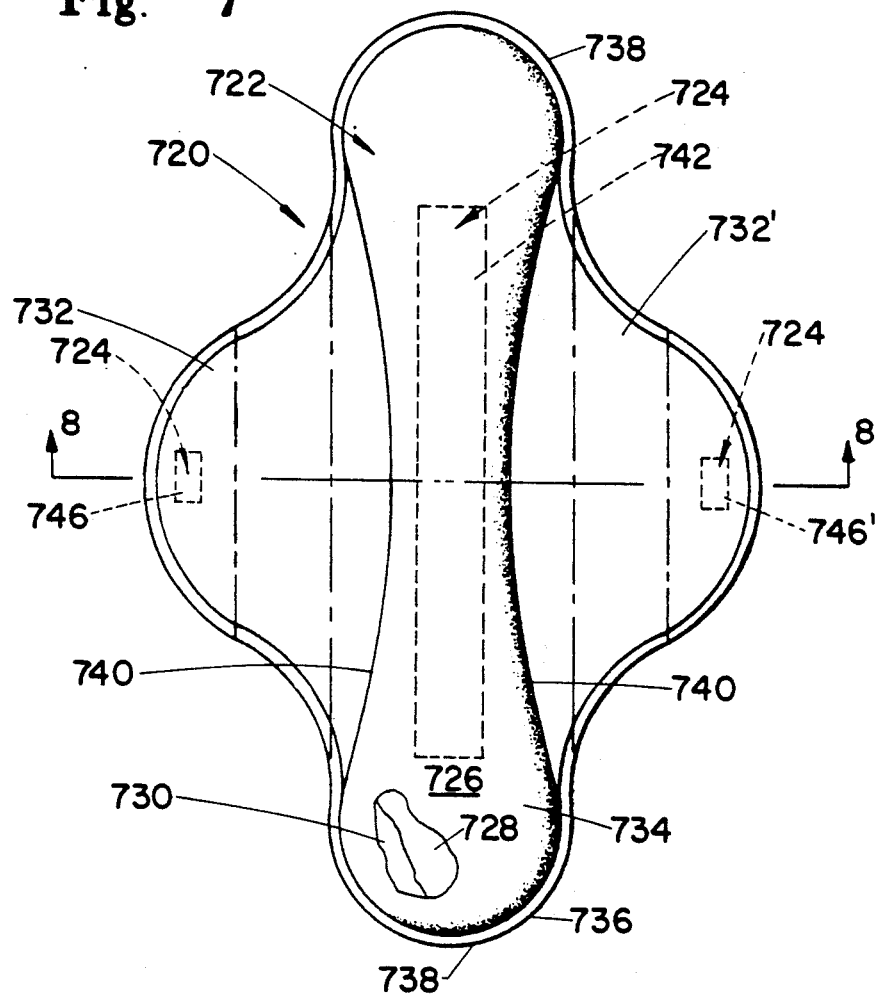
FIG. 7 is a partially cut-away plan view of a sanitary napkin embodying the pressure-sensitive adhesive fastener of the present invention.

FIG. 7 shows an alternative embodiment of the present invention wherein the disposable absorbent article is a sanitary napkin 720 designed to receive and contain vaginal discharges such as menses. Disposable sanitary napkins are designed to be held adjacent to the human body through the agency of a garment, such as an undergarment or a panty or by a specially designed belt. Examples of the kinds of sanitary napkins to which the present invention is very readily adapted are shown in U.S. Pat. No. 4,687,478 entitled "Shaped Sanitary Napkin With Flaps which issued to Kees J. Van Tilburg on Aug. 18, 1987; U.S. Pat. No. 4,589,876 entitled "Sanitary Napkin" which issued to Kees J. Van Tilburg on May 20, 1986; U.S. Pat. No. 4,681,578 entitled "Pantiliner With Ventilation Areas" which issued to Arthur B. Anderson and Sherry L. Brandt on Jul. 21, 1987; and U.S. Pat. No. 4,690,680 entitled "Adhesive Attachment Means for Absorbent Articles" which issued to Maureen L. Higgins on Sep. 1, 1987. Each of these patents are herein incorporated by reference. It will be apparent from the following description that the fastening system illustrated and described herein may be applied to such sanitary napkins. On the other hand, it will be understood the present invention is not limited to any specific sanitary napkin structure or configuration. FIG. 7 is a plan view of a sanitary napkin 720 embodying the present invention prior to it being placed in the undergarment of the wearer. As can be shown in FIG. 7, a preferred sanitary napkin construction comprises a body portion 722 and a fastening system 724.

A preferred body portion 722 comprises a liquid pervious topsheet 726, an absorbent core 728, and a liquid impervious backsheet 730. While the topsheet 726, the absorbent core 728, and the backsheet 730 may be assembled in a variety of well-known configurations, a preferred sanitary napkin configuration is shown and described generally in the above-referenced U.S. Pat. No. 4,687,478 which issued to Kees J. Van Tilburg on Aug. 18, 1987, and which patent is incorporated herein by reference, wherein the sanitary napkin 720 has flaps 732 and 732'.

The body portion 722 has an inside surface 734 and an outside surface 736. In general, the outside surface 736 of the body portion 722 extends from one end edge 738 to the other end edge 738 of the body portion 722 and from one longitudinal edge 740 to the other longitudinal edge 740 of the body portion 722 and is the surface farthest from the wearer during use of the sanitary napkin 720 and is designed to fit adjacent the undergarment of the wearer. When a backsheet 730 is used, it typically forms the outside surface 736 of the body portion 722. The inside surface 734 is that surface of the body portion 722 opposite the outside surface 736 and in the embodiment shown is typically formed by the topsheet 726. In general, the inside surface 734 of the body portion is that surface coextensive with the outside surface 736 and which is for the greater part in contact with the wearer when the sanitary napkin 720 is worn.

The sanitary napkin 720 is provided with a fastening system 724 for securing the sanitary napkin 720 to the undergarment of the wearer.

Figure 8:
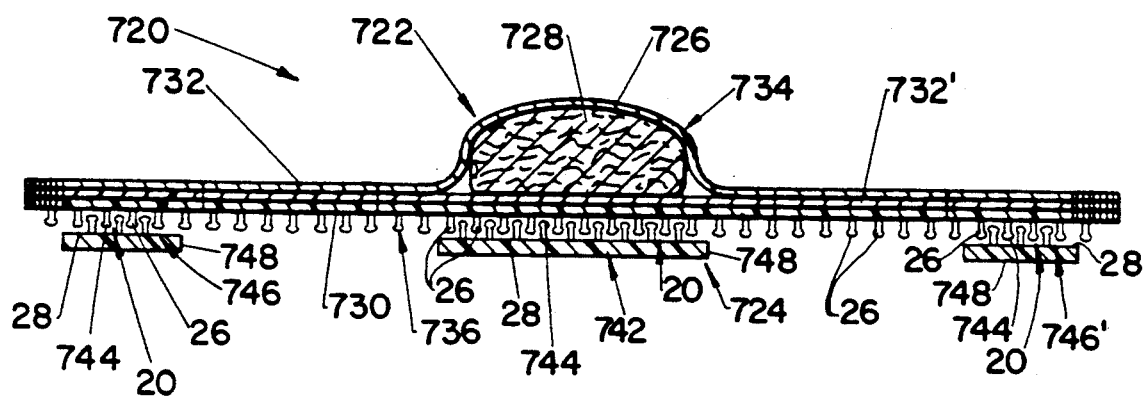
FIG. 8 is a sectional view taken along line 8—8 of FIG. 7.

In a preferred embodiment of the present invention as shown in FIG. 8, the fastening system 724 comprises an attachment member 742 positioned on the outside surface 736 of the body portion 722 of the sanitary napkin 720 and a release liner 748 releasably attached to the adhesive of the attachment member 742. The attachment member 742 comprises a fastening element 744 comprising the pressure-sensitive adhesive fastener 20 of the present invention. The fastening element 744 may be a discrete, separate member secured to the outside surface 736 of the body portion 722, or a unitary member than is neither divided nor discontinuous with an element of the sanitary napkin 720 such as the backsheet 730. In the preferred embodiment shown in FIG. 8, the backsheet 730 serves as the backing web 24 of the pressure-sensitive adhesive fastener 20 such that the fastening element 744 is unitary with the backsheet 730. The pressure-sensitive adhesive fastener 20 is typically formed by coating the outer surface of the backing web/backsheet with a layer o pressure-sensitive adhesive 28.

The exact pattern of adhesive on the fastening element 744 may widely vary and take on a number of configurations such as an array of discrete elements. For example, the fastening element 744 may comprise a multiplicity of discrete elements such as strips, circles, triangles, or any other shapes arranged in either a random or regular pattern which provides a zone or zones of adhesion. While the size, arrangement, and disposition of the fastening element(s) on the outer surface may vary, the fastening element 744 preferably comprises a relatively wide rectangular shaped layer of pressure-sensitive adhesive that extends longitudinally along the body portion 722.

In use, the sanitary napkin 720 is secured on the inside of the crotch portion of an undergarment with the pressure-sensitive adhesive fastener side of the sanitary napkin 720 toward the crotch portion of the undergarment. Thus, the undergarment serves as the landing member for the fastening system 724. The release liner 748 is removed from the attachment member 742 and the sanitary napkin 720 is secured in position by pressing the exposed pressure-sensitive adhesive fastener 20 firmly against the crotch material of the undergarment. The bulbous surface aberrations 26 of the pressure-sensitive adhesive fastener 20 will engage certain fibers of the undergarment and be secured thereto by the pressure-sensitive adhesive layer 28 to provide a secure attachment of the sanitary napkin 720 within the undergarment.

Since a preferred embodiment of the sanitary napkin 720 of the present invention comprises flaps 732 and 732', a flap attachment member 746 is also provided on one or both of the flaps 732 and 732' to maintain the flaps 732 and 732' in position after the flaps 732 and 732' have been wrapped around the edge of the crotch portion of the undergarment. A release liner 748 is positioned over each of the flap attachment members 746 to protect the adhesive until the sanitary napkin 720 is used, the release liner being removed and the flap being wrapped around the edge of the crotch portion of the undergarment. The flap attachment members 746 each preferably comprise the fastening element 744 previously described that forms the attachment member 742 of the body portion 722. Thus, the flap attachment members 746 each preferably comprise the pressure-sensitive adhesive fastener 20 of the present invention. As shown in FIG. 8, the flap attachment members 746 thus each comprise the fastening elements 744 that are unitary with the backsheet 730.

While particular embodiments of the present invention have been illustrated and described, it would be obvious to those skilled in the art that various other changes and modifications can be made without departing from the spirit and scope of the invention. It is therefore intended to cover in the appended claims all such changes and modifications within the scope of this invention.

What is claimed is:

1. A disposable absorbent article comprising:
a body portion comprising a topsheet, a backsheet joined to said topsheet, and an absorbent core positioned between said topsheet and said backsheet; and
a fastening system attached to said body portion, said fastening system comprising a fastening element comprising
(i) a backing web having a first surface and a second surface, said backing web having discrete, bulbous surface aberrations projecting from said first surface, at least some of said bulbous surface aberrations having an end portion and a base portion, said end portion comprising at least one microbubble substantially coinciding with the point of maximum amplitude of said bulbous surface aberration, said microbubble and said base portion of said bulbous surface aberrations each having walls, said microbubble comprising a flexible membrane joined about its periphery to said base portion, and said walls of said microbubble being thinner than the walls of said base portion of said bulbous surface aberration, and
(ii) a layer of pressure-sensitive adhesive coated over and bonded to at least a portion of the surface of some of said bulbous surface aberrations.

2. The absorbent article of claim 1 wherein said microbubble comprises a continuous membrane.

3. The absorbent article of claim 2 wherein said pressure-sensitive adhesive is coated over and bonded to said first surface of said backing web.

4. A disposable diaper comprising:
a body portion having an inside surface, an outside surface, longitudinal edges, a first end region, and a second end region, said portion comprising a liquid pervious topsheet, a liquid impervious backsheet joined to said topsheet, and an absorbent core positioned between said topsheet and said backsheet; and
a fastening system positioned on said body portion for maintaining said first end region and said second end region in an overlapping configuration during use, said fastening system comprising:
(a) a closure member disposed adjacent each longitudinal edge in said first end region, said closure member comprising a first fastening element comprising
(i) a backing web having a first surface and a second surface, said backing web having discrete, bulbous surface aberrations projecting from said first surface, at least some of said bulbous surface aberrations having an end portion and a base portion, said end portion comprising at least one microbubble substantially coinciding with the point of maximum amplitude of said bulbous surface aberration, said microbubble and said base portion of said bulbous surface aberrations each having walls, said microbubble comprising a flexible membrane joined about its periphery to said base portion, and said walls of said microbubble being thinner than the walls of said base portion of said bulbous surface aberration, and
(ii) a layer of pressure-sensitive adhesive coated over and bonded to at least a portion of the surface of some of said bulbous surface aberrations; and
(b) at least one landing member disposed in said second end region, said landing member having a textured contacting surface engageable with said bulbous surface aberrations of said first fastening element.

5. The diaper of claim 4 wherein said layer of pressure-sensitive adhesive is coated over and bonded to said first surface of said backing web.

6. The diaper of claim 5 wherein said landing member is positioned on said outside surface in said second end region.

7. The diaper of claim 6 wherein said textured contacting surface of said landing member exhibits a pattern of discrete, bulbous surface aberrations engageable with said bulbous surface aberrations of said first fastening element.

8. The diaper of claim 7 wherein said landing member is unitary with said backsheet.

9. The diaper of claim 7 wherein said landing member additionally comprises a layer of pressure-sensitive adhesive coated over and bonded to at least a portion of the surface of said bulbous surface aberrations.

10. The diaper of claim 9 wherein said landing member comprises a discrete, separate element affixed to said backsheet.

11. The diaper of claim 9 wherein said landing member is unitary with said backsheet.

12. The diaper of claims 6, 7, 9 or 11 wherein each of said closure members comprises an inner fastening member positioned on said inside surface of said body portion.

13. The diaper of claims 6, 7, 9 or 11 wherein each of said closure members comprises a tape tab disposed adjacent each longitudinal edge of the diaper in said first end region, each of said tape tabs having a fastening surface and a backing surface, said first fastening element being disposed on said fastening surface.

14. The diaper of claim 13 wherein said first fastening element is a discrete, separate member joined with said tape tabs.

15. A disposable diaper comprising:
a body portion having an inside surface, an outside surface, longitudinal edges, a first end region, and a second end region, said portion comprising a liquid pervious topsheet, a liquid impervious backsheet joined to said topsheet, and an absorbent core positioned between said topsheet and said backsheet; and
a fastening system for maintaining said first end region and said second end region in an overlapping configuration during use, said fastening system comprising:
(a) a tape tab disposed adjacent each longitudinal edge in said first end region, said each of said tape tabs comprising
a first fixed portion,
first tab attachment means associated with said first fixed portion and said inside surface of said body portion for attaching said first fixed portion to said inside surface,
a second fixed portion,
second tab attachment means associated with said second fixed portion and said inside surface of said body portion for attaching said second fixed portion to said outside surface,
a connective portion having a fastening surface and a backing surface,
a first fastening element joined on at least a portion of said fastening surface of said connective portion for attaching said connective portion to said body portion, said first fastening element comprising (i) a backing web having a first surface and a second surface, said backing web comprising a polymeric material, said backing web having discrete, bulbous surface aberrations projecting from said first surface, at least some of said bulbous surface aberrations having an end portion and a base portion, said end portion comprising at least one microbubble substantially coinciding with the point of maximum amplitude of said bulbous surface aberration, said microbubble and said base portion of said bulbous surface aberrations each having walls, said microbubble comprising a flexible, continuous membrane joined about its periphery to said base portion, said walls of said microbubble being thinner than the walls of said base portion of said bulbous surface aberration, and (ii) a layer of pressure-sensitive adhesive coated over and bonded to said first surface of said backing web, and
said first fixed portion, said second fixed portion and said connective portion attached in an area of joinder adjacent said longitudinal edge of said body portion; and
(b) at least one landing member disposed on said outside surface in said second end region, said landing member having a textured contacting surface, said landing member having discrete, bulbous surface aberrations, said bulbous surface aberrations being engageable with said bulbous surface aberrations of said first fastening element.

16. The diaper of claim 15 wherein said landing member additionally comprises a layer of pressure-sensitive adhesive coated over and bonded to said contacting surface of said landing member.

17. The diaper of claim 15 or 16 wherein said landing member is a discrete, separate element affixed to said backsheet.

18. The diaper of claims 15 or 16 wherein said landing member is unitary with said backsheet.

19. The diaper of claim 18 wherein said connective portion is unitary with said second fixed portion.

20. A sanitary napkin comprising:
a body portion having an inside surface, an outside surface, longitudinal edges, and said body portion comprising a liquid pervious topsheet, a liquid impervious backsheet joined to said topsheet, and an absorbent core positioned between said topsheet and said backsheet; and
a fastening system positioned on said outside surface of said body portion, said fastening system comprising an attachment member
(i) a backing web having a first surface and a second surface, said backing web having discrete, bulbous surface aberrations projecting from said first surface, at least some of said bulbous surface aberrations having an end portion and a base portion, said end portion comprising at least one microbubble substantially coinciding with the point of maximum amplitude of said bulbous surface aberration, said microbubble and said base portion of said bulbous surface aberrations each having walls, said microbubble comprising a flexible membrane joined about its periphery to said base portion, said walls of said microbubble being thinner than the walls of said base portion of said bulbous surface aberrations, and
(ii) a layer of pressure-sensitive adhesive coated over and bonded to at least a portion of the surface of said bulbous surface aberrations.

21. The sanitary napkin of claim 20 wherein said pressure-sensitive adhesive is coated over and bonded to said first surface of said backing web.

22. The sanitary napkin of claim 21 additionally comprising flaps extending laterally outwardly from each longitudinal edge of said body portion, said fastening system additionally comprising a flap attachment member associated with at least one of said flaps, said flap attachment member comprising said fastening element.

23. The sanitary napkin of claim 22 wherein said fastening system comprises a flap attachment member positioned on each of said flaps.

24. The sanitary napkin of claims 21, or 23 wherein said fastening elements are unitary with said backsheet.

* * * * *

UNITED STATES PATENT AND TRADEMARK OFFICE
CERTIFICATE OF CORRECTION

PATENT NO. : 5,221,276
DATED : June 22, 1993
INVENTOR(S) : CHARLES FREDERICK BATTRELL It is certified that error appears in the above-identified patent and that said Letters Patent is hereby corrected as shown below:

Column 6, line 64, "261" should read --26--.

Column 10, line 56, "than o the" should read --than the--.

Column 16, line 11, "region" should read --regions--.

Column 16, line 24, "BO" should read --80--.

Column 19, line 31, "wearer s" should read --wearer's--.

Column 20, line 56, "layer o" should read --layer of--.

Column 22, line 14, "said portion" should read --said body portion--.

Column 23, line 22, "said portion" should read --said body portion--.

Column 23, line 32, "region, said each" should read --region, each--.

Column 23, line 41, "inside" should read --outside--.

Signed and Sealed this

Sixteenth Day of April, 1996

Attest:

BRUCE LEHMAN

*Attesting Officer*  *Commissioner of Patents and Trademarks*